US00PP09387P

United States Patent [19]

Iverson

[11] Patent Number: Plant 9,387

[45] Date of Patent: Nov. 28, 1995

[54] DAYLILY PLANT NAMED 'X-2'

[76] Inventor: Ronald C. Iverson, Rte. 1, Box 326B, Orange, Va. 22960

[21] Appl. No.: 355,318

[22] Filed: Dec. 12, 1994

[51] Int. Cl.[6] ..... A01H 5/00

[52] U.S. Cl. ..... Plt./87.4

[58] Field of Search ..... Plt./87.4

*Primary Examiner*—James R. Feyrer

*Attorney, Agent, or Firm*—Foley & Lardner

[57] ABSTRACT

A new cultivar of daylily plant named X-2, characterized by its large frilly double flowers with petals which are apricot in color at the tip, blending into a deeper yellow-orange which merges into a bright yellow throat, recurved petals with crimped edges, fragrant flowers, reblooming ability, and its floriferous habit.

2 Drawing Sheets

The present invention comprises a new and distinct cultivar of daylily which belongs to the genus Hemerocallis, and is hereinafter referred to by the cultivar name X-2.

The new cultivar is the result of an open pollination breeding program in which numerous unnamed and unidentified daylily cultivars were planted in an open cultivated field in a controlled environment in Merriville, Ind. Seed was collected from the open pollinated female plants and grown in a controlled area in Merriville, Ind.

Well over one thousand seedling plants were mass-selected in early summer 1990, and grown out in Long Grove, Ill. in a cultivated area. The new cultivar was discovered and selected from the mass-selected plants by inventor Ronald C. Iverson in August 1980 in such area in Long Grove, Ill.

The first act of asexual reproduction of the new cultivar was accomplished when divisions were taken from the selection in September 1990 in a controlled environment in Long Grove, Ill. by Ronald C. Iverson. Horticulture examination of selected units initiated in June 1991 has demonstrated that the combination of characteristics as herein disclosed for the new cultivar are firmly fixed and are retained through successive generations of asexual reproduction.

The new cultivar X-2 has not been observed under all possible environmental conditions. The phenotype may vary significantly with variations in environment such as temperature, light intensity, and daylength without, however, any variance in genotype. The following observations, measurements, and comparisons describe plants grown in Long Grove, Ill. under greenhouse conditions which approximate those generally used in commercial practice.

The following traits have been repeatedly observed and are determined to be basic characteristics of X-2 which in combination distinguish this daylily as a new and distinct cultivar.

1. The petal color near the tip is apricot, blending to a deeper yellow-orange which merges into a bright yellow throat.

2. Flowers are very fragrant.

3. Flowers are very frilly and veins are indented on surface.

4. Individual flowers are large, approximately 4½ inches in diameter, and have 12 petals thereby providing a double flower with a very full look.

5. There are an average of 15 buds on a flower scape, making the cultivar floriferous.

6. Individual fans produce 2–3 flowering scapes in each season. This ability to rebloom is a significant feature of the new cultivar.

The accompanying color photographic drawings show typical flower characteristics of X-2, with colors being as true as possible with illustrations of this type.

The photo on sheet 1 is a top perspective view of a typical plant of the new cultivar grown in a 10 inch pot.

The photo on sheet 2 is a greatly enlarged top view showing in much greater detail the flower parts.

In the following description, color references are made to the Royal Horticultural Society Colour Chart. The color values were determined between 11:30 a.m. to 12:30 p.m. on June 30 under hazy light conditions at Long Grove, Ill.

Parentage:

*Origin.*—Selection from mass-selected seedling population obtained by open pollination.

*Parentage.*—Seed parent: Unknown. Pollen parent: Unknown.

Classification:

*Botanic.*—Hemerocallis hybrid

*Commercial.*—Large flower daylily cv. X-2.

Plant description:

*Form.*—Wide, spreading.

*Height.*—Approximately 18 inches.

*Growth habit.*—Clump forming, vigorous.

*Strength.*—Good.

*Foliage.*—Size of leaf: 1½ inches wide by 20 inches long. Shape of leaf: Typical Hemerocallis. Texture: Fine to medium. Color: Green 144A.

*Bulbs.*—Size: 6 inches long. Color: Tan.

Bud description:

*Form.*—Columnar.

*Size.*—2½ inches long.

*Opening.*—Early morning.

*Color.*—Green.

Flowering description:

*Blooming habit.*—Early July until October.

*Size.*—Large, 4½ inches in diameter.

*Borne.*—15° angle from the scape, on ¾ inch peduncle lime green in color.

*Shape.*—Star.

*Tepalage.*—Number of tepals: 12, flower is double. Color: Upper surface: Tip is 19C blending through 16B to 5A throat. Lower surface: 24C. Tepal longevity: One day. Spotting: No markings. Color change: There is no or very little fading of color in bright sunlight on hot days. Texture: Wrinkled, edges crimped ¼ inch. Appearance: Petals recurve back ¾ inch; inner petals very frilly; veins are deep on upper surface of petals and somewhat darker than main color. Disease resistance: No recognized problems. Fragrance: Very fragrant. Lasting quality: One day.

Reproductive organs:

*Stamens, anthers.*—Arrangement: All modified into petals. Number: Six. Pollen: Small amount, color 7A.

*Pistils.*—Three inches in length.

Fruit:

*Fertility.*—Very low.

*Color at maturity.*—Black.

I claim:

1. A new and distinct cultivar of daylily plant named X-2, as illustrated and described.

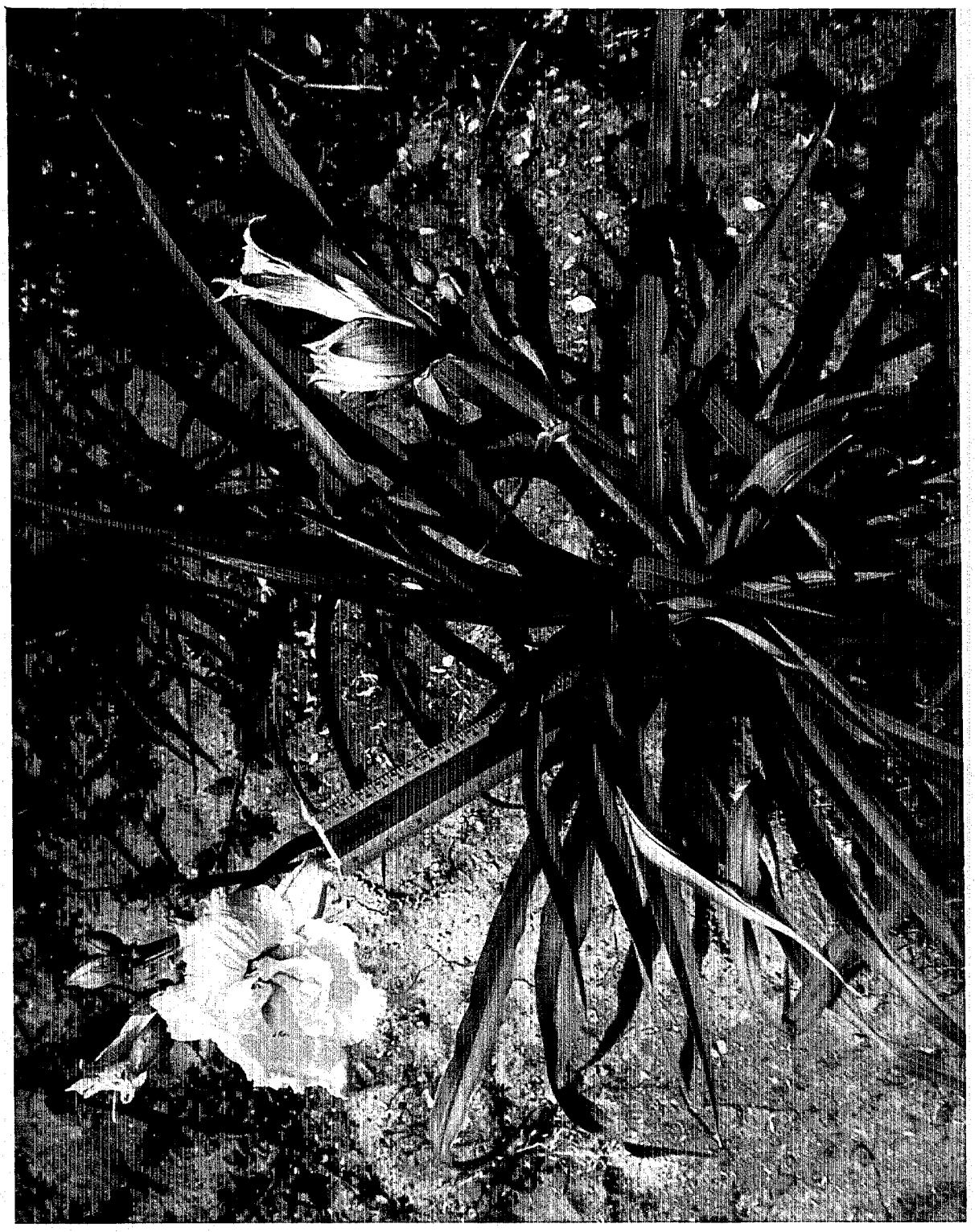

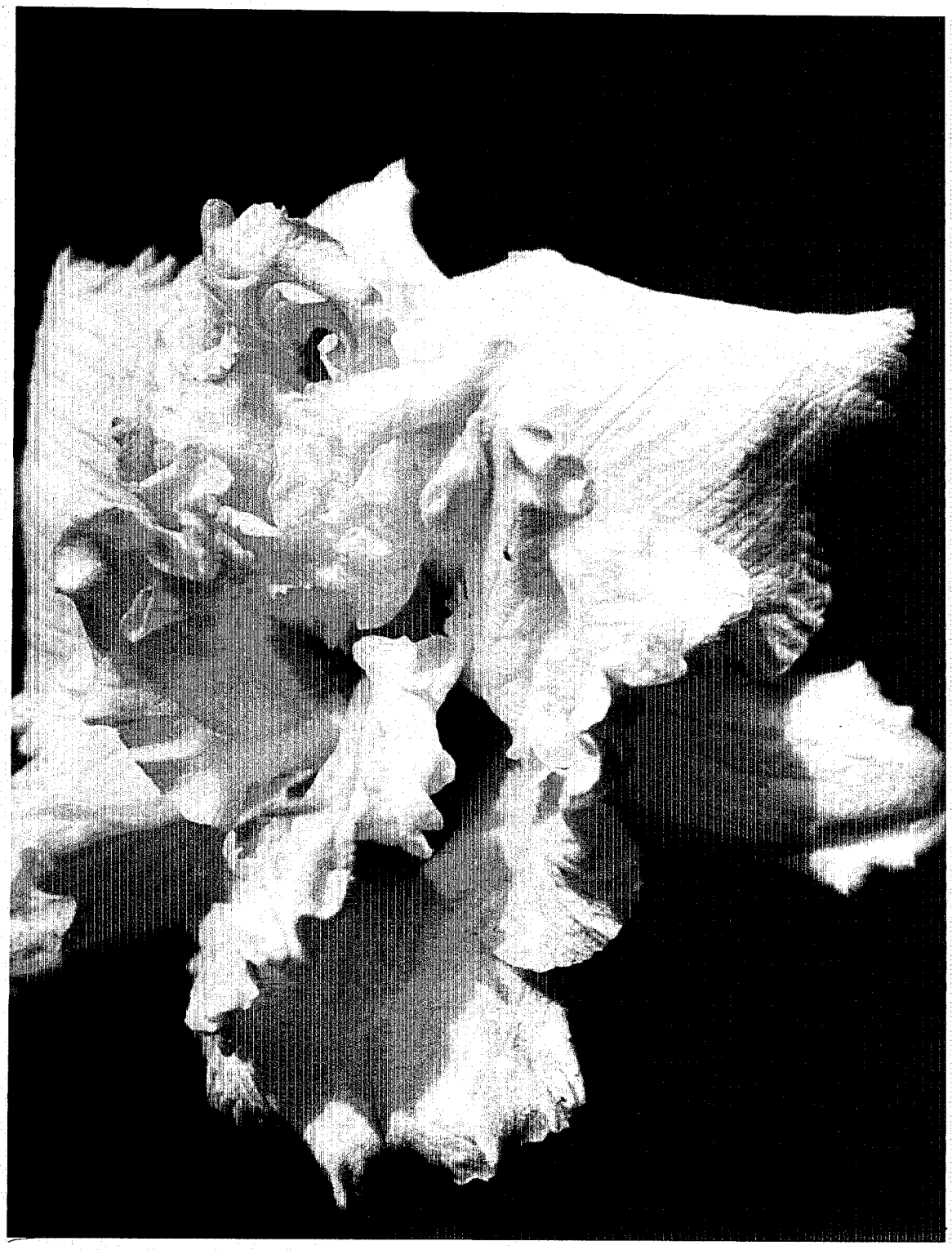

* * * * *